(12) United States Patent
Hong et al.

(10) Patent No.: US 8,053,250 B2
(45) Date of Patent: Nov. 8, 2011

(54) METHOD AND SYSTEM FOR SUPPRESSING BINDINGS ON MAGNETIC PARTICLES

(76) Inventors: Rex Chin-Yih Hong, Taipei (TW); Herng-Er Horng, Taipei (TW); Hong-Chang Yang, Taipei (TW); Shieh-Yueh Yang, Taipei County (TW)

(*) Notice: Subject to any disclaimer, the term of this patent is extended or adjusted under 35 U.S.C. 154(b) by 527 days.

(21) Appl. No.: 12/163,313

(22) Filed: Jun. 27, 2008

(65) Prior Publication Data

US 2009/0325317 A1 Dec. 31, 2009

(51) Int. Cl.
*G01N 33/533* (2006.01)
(52) U.S. Cl. ........................................................ 436/526
(58) Field of Classification Search .................. 436/526
See application file for complete search history.

(56) References Cited

U.S. PATENT DOCUMENTS

| 6,346,196 B1* | 2/2002 | Bose .................. 210/695 |
| 2002/0009759 A1* | 1/2002 | Terstappen et al. ........... 435/7.23 |
| 2006/0205093 A1* | 9/2006 | Prins .............................. 436/526 |

FOREIGN PATENT DOCUMENTS

| WO | WO 03/019188 | 3/2003 |
| WO | WO 2005/010527 | 2/2005 |

OTHER PUBLICATIONS

J. Roger et al., "Some biomedical applications of ferrofluids" The European Physical Journal Applied Physics, Mar. 1, 1999, vol. 5, No. 3, pp. 321-325.
European Search Report of European Application No. 09251627.7—2204, dated Sep. 21, 2009.

* cited by examiner

*Primary Examiner* — Mark Shibuya
*Assistant Examiner* — Pensee Do
(74) *Attorney, Agent, or Firm* — J.C. Patents

(57) ABSTRACT

A method for suppressing non-specific bindings between molecules includes providing magnetic particles dispersed in a liquid, wherein each of the magnetic particles has a magnetization. The magnetic particles are coated with coating molecules. Binding molecules mixed of first-type binding molecules and second-type binding molecules are applied to the liquid, wherein the coating molecules are specifically binding with the first-type binding molecules and non-specifically binding with the second-type binding molecules. An alternating current (ac) magnetic field is applied at an axis with a frequency level, wherein the frequency level causes suppression of the second-type binding molecules in binding with the coating molecules.

11 Claims, 4 Drawing Sheets

METHOD AND SYSTEM FOR SUPPRESSING BINDINGS ON MAGNETIC PARTICLES

BACKGROUND OF THE INVENTION

1. Field of Invention

The present invention relates to measuring magnetic susceptibility of material. More particularly, the present invention relates to suppress non-specific bindings on magnetic particles based on investigation on magnetic susceptibility of magnetic material.

2. Description of Related Art

In chemical industry, it is often to produce composite molecules which include several kinds of molecules bound together. In medicine production as an example, several molecules should be mixed together to have the curing effect. However, during mixing the molecules, some un-wanted molecules may be also bound as well, causing impurity or even producing the other effect. Usually, the specific binding molecules are wanted while the non-specific binding molecules are unwanted.

How to suppress the non-specific binding molecules and even increase the specific binding molecules to a core particle is an issue in the art, so as to suppress the non-specific binding molecules.

SUMMARY OF THE INVENTION

The invention is directed to forming composed molecules, in which the non-specific bindings can be reduced based on properties of the alternating current (ac) magnetic susceptibility $\chi_{ac}$.

The invention provides a method for suppressing non-specific bindings between molecules including providing magnetic particles dispersed in a liquid, wherein each of the magnetic particles has a magnetization. The magnetic particles are coated with coating molecules. Binding molecules mixed of first-type binding molecules and second-type binding molecules are applied to the liquid, wherein the coating molecules are specifically binding with the first-type binding molecules and non-specifically binding with the second-type binding molecules. An ac magnetic field is applied with a frequency level, wherein the frequency level causes suppression of the second-type binding molecules in binding with the coating molecules.

The present invention also provides a system to suppress non-specific bindings on magnetic particles. The system comprises a container filled with a liquid dispersed with magnetic particles, wherein each of the magnetic particles has a magnetization and is coated with coating molecules to bind with binding molecules, wherein the binding molecules includes first-type binding molecules and second-type binding molecules, and the coating molecules are specifically binding with the first-type binding molecules and non-specifically binding with the second-type binding molecules. An ac magnetic field source unit applies an ac magnetic field on the liquid in the container with a frequency level, wherein the frequency level is set to suppress the second-type binding molecules in binding with the coating molecules.

It should be understood that both the proceeding general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

In the invention, an ac magnetic susceptibility $\chi_{ac}$ is used as an investigating tool to suppress the non-specific molecules to the core molecules while the specific binding molecules can remain or even increase to bind on the core molecules. The core molecules have magnetization.

The method to suppress the non-specific binding between molecules is developed. By coating one kind of molecules (referred as CM molecules) onto magnetic material particles having magnetization, that is a total magnetic vector from the magnetic dipoles. The magnetic particles are dispersed in a liquid, the coated molecules can bind with other kinds of molecules (referred as BM molecules) specifically or non-specifically. This is one of helpful manner to form composite molecules, such as medicine materials. However, usually, the non-specifically binding molecules are unwanted material and should be suppressed.

In the basic mechanism of the present invention, when ac magnetic fields are applied, magnetic vectors rotate under the drive of ac magnetic fields. Thus, the BM molecules suffer with a centrifugal force. As the centrifugal force exceeds the binding force between the CM molecules and the BM molecules, these CM-BM molecular binding is broken. Since the binding force for specific binding is much higher than that of non-specific binding, the non-specific binding can be depressed by suitably controlling the centrifugal force. In case, the centrifugal force can be controlled by manipulating the angular frequency of rotating magnetic vectors, which is determined by the frequency of the applied ac magnetic fields. Therefore, by well controlling the frequency of applied ac magnetic fields, non-specific bindings between molecules can be efficiently suppressed.

Before describing how to actually measure the X ac as to be described later in FIGS. 3-5, the mechanism to suppress the non-specific binding molecules is described first.

Figure 1:
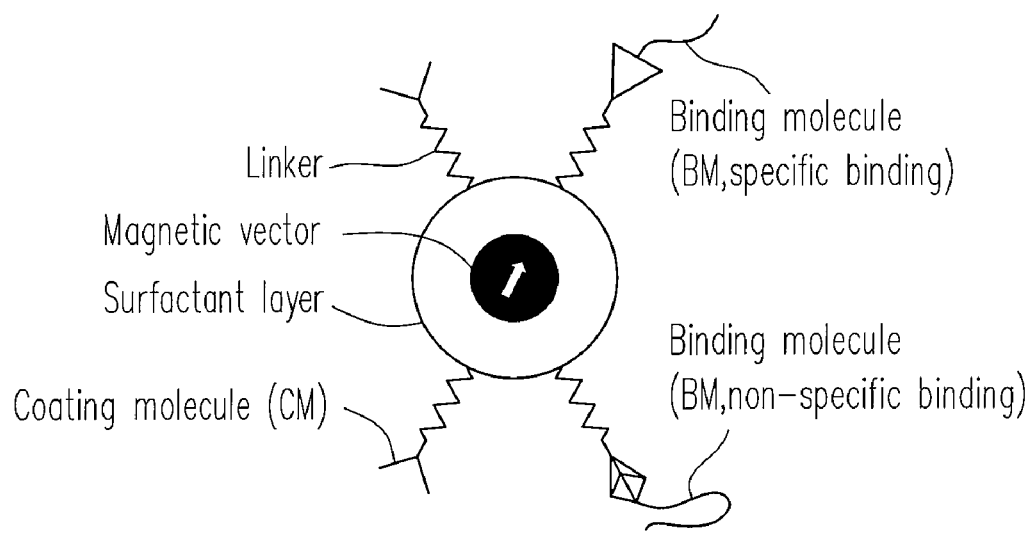
FIG. 1 is a drawing, schematically illustrating the binding mechanism between the magnetic particles and the binding molecules for specific bindings and non-specific bindings, according to the present invention.

FIG. 1 is a drawing, schematically illustrating the binding mechanism between the magnetic particles and the binding molecules for specific bindings and non-specific bindings, according to the present invention. Some coating molecules (CM) are to be coated onto magnetic particles, which have magnetic vectors. Taking one magnetic particle as an example for descriptions, the core particle with magnetic particle has the magnetization vector as shown an arrow. The magnetic particle is coated with a surfactant layer, so that the magnetic particles can be dispersed in a liquid. A linker as one kind of molecules is coated onto the surfactant layer. As schematically shown in FIG. 1, the coated molecules, or linker, are referred as CM molecules. The linker can be primary bindings such as covalent binding or antibody-antigen conjugation binding, or nuclei-acid hybridization, etc. Thus, the CM molecules can be firmly coated onto the surfactant layer of magnetic vectors. The surfactant layer is hydrophilic. When a solution having specific and non-specific binding molecules (hereafter referred as BM molecules) is mixed with the aqueous solution of magnetic vectors coated with CM molecules, both specific and non-specific BM molecules bind with CM molecules. However, the binding force between CM molecules and non-specific BM molecules is much weaker than that between CM molecules and specific BM molecules. Thus, when a force (hereafter referred as against force), which strength is higher/lower than the binding force between CM molecules and non-specific/specific BM molecules, is applied, it is possible to break/keep the binding between CM molecules and non-specific/specific BM molecules. Therefore, the non-specific binding can be efficiently suppressed.

About mechanism for generating the against force, since magnetic vectors are dispersed in liquid, the motion of magnetic vectors can be manipulated by applying magnetic fields to the liquid, such as applying ac magnetic field. In physic phenomenon, the magnetic vectors interact with the externally applied magnetic filed and the magnetic vectors are in parallel with the magnetic field. When the ac magnetic field is applied, the amplitude of the magnetic filed is oscillating. The magnetic dipoles of the magnetic particles are driven by the ac magnetic field in parallel. Due to oscillation of the ac magnetic filed, the magnetic dipoles rotate in resonant with the ac magnetic fields. When a magnetic vector rotates at the plane having the oscillating axis, a centrifugal force is generated to against the CM-BM molecular binding. In case, the centrifugal force acts as against force. Theoretically, the centrifugal force is proportional to the square of the angular frequency of the rotation of magnetic vectors. Thus, by choosing a suitable frequency for the applied magnetic fields, the strength of against force can be higher than the CM-non-specific-BM molecular bind, but lower than the CM-specific-BM molecular binding. As a result, the non-specific binding can be suppressed.

In order to further investigate the foregoing phenomena, some experiments are performed. The magnetic particles can be, for example, $Fe_3O_4$ magnetic nanoparticles. The mean diameter of magnetic nanoparticles can range, for example, from few nm's to hundreds of nm's. The material of magnetic nanoparticles can also, for example, be either of $MnFe_2O_4$, $Fe_2O_3$, $NiFe_2O_4$ or $CoFe_2O_4$. The surfactant layer is, for example, dextran. The CM molecule is, for example, polyclonal antibody like anti-H1N2, which show specific binding to H1N2 and non-specific binding to H3N1. The linker is, for example, a form of the covalent binding —CH=N—. For example, the linker can be generated by oxiding dextran to create aldehyde groups (—CHO) on dextran, followed by reacting with antibody to form —CH=N— between dextran and antibody. The material of the surfactant layer can also be either of dextran, protein G, protein A, liposomes or organic acids.

Figure 2:
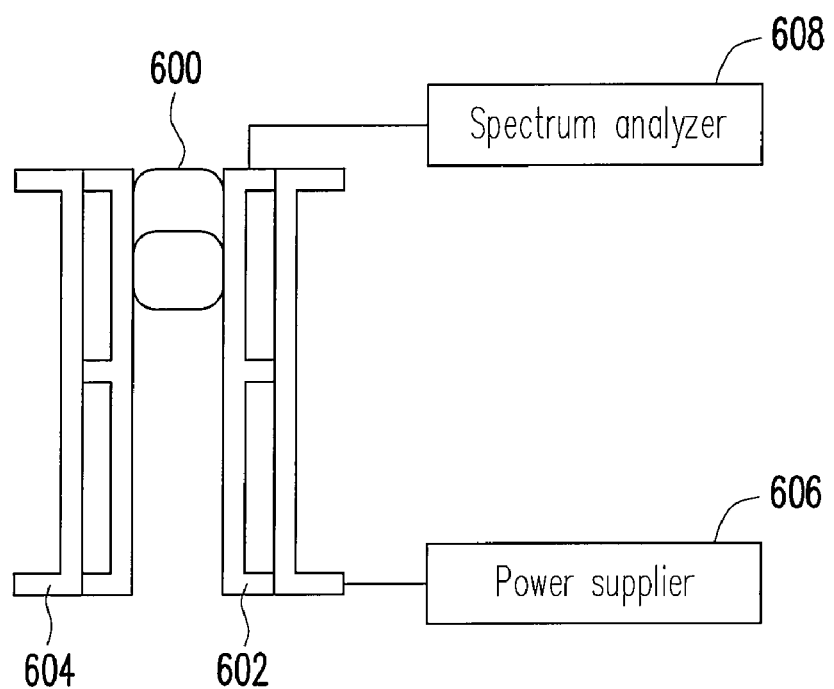
FIG. 2 is a drawing, schematically illustrating a system to measure the ac magnetic susceptibility of a sample, according to an embodiment of the present invention.

FIG. 2 is a drawing, schematically illustrating a system for measuring the ac magnetic susceptibility of a sample, according to an embodiment of the present invention. The excitation magnetic field(s) to rotate magnetic nanoparticles is generated with excitation coils driven with power suppliers, as schematically shown in FIG. 2. The power supplier 606 can provide ac currents of various frequencies to the excitation coil 604. Thus, the excitation coil 604, such as solenoid coil, can generate excitation magnetic field of various frequency. As mentioned, the centrifugal force (i.e. against force) becomes stronger at higher frequencies of the ac excitation magnetic fields. Hence, by adjusting the frequency of the driving current of the excitation oil 604, the against force can be manipulated. The ac magnetic filed is generated within excitation oil 604 at the central axis. The ac magnetic signals of rotating magnetic nanoparticles (hereafter referred as ac magnetic susceptibility $\chi_{ac}$) are sensed with pick-up coils 602, and analyzed with a spectrum analyzer 608. The pick-up coil 602 for example includes two sets of solenoids wired at opposite directions to eliminate the contributions from the applied ac magnetic field to $\chi_{ac}$. The sample 600, such as a container to hold the liquid, is posited inside one of the two solenoids of the pick-up coil 602.

For investigating the specific binding, the BM molecule is H1N2. The binding between anti-H1N2 and H1N2 is measured via magnetoreduction assay. 40-μl and 0.1-emu/g magnetic reagent bio-functionalized with anti-H1N2 is mixed with 60-ul and 3.2-HAU/50 μl H1N2 test solution. At lower rotating frequency, say 500 Hz, the magnetic susceptibility (referred as $\chi_{ac,o}$) of sample before the formation of the specific binding between anti-H1N2 and H1N2 was measured.

Figure 3:
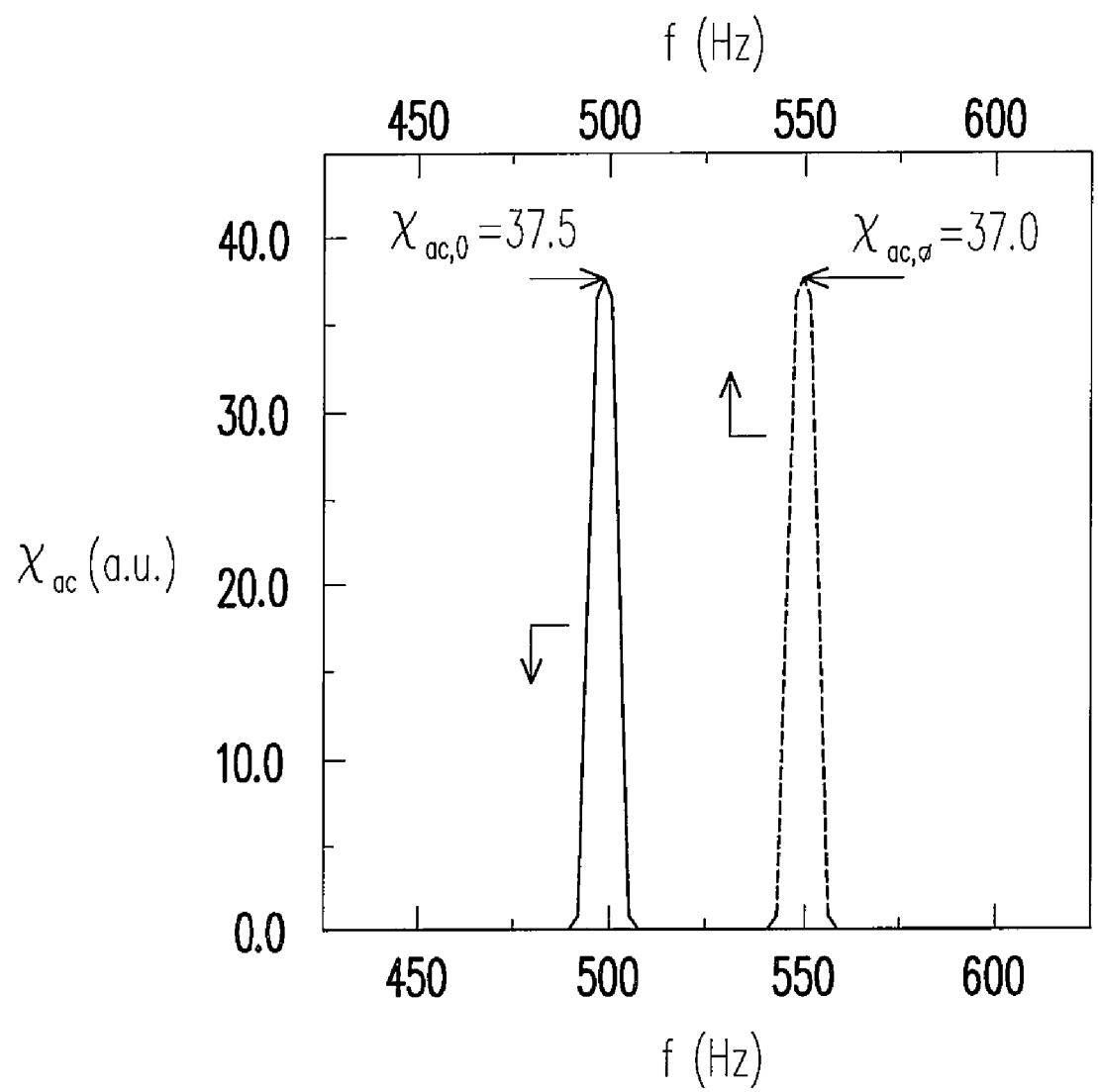
FIGS. 3-5 are drawings, schematically illustrating the phenomena in relation of $\chi_{ac}$ with the specific binding molecules and non-specific binding molecules.
Figure 4:
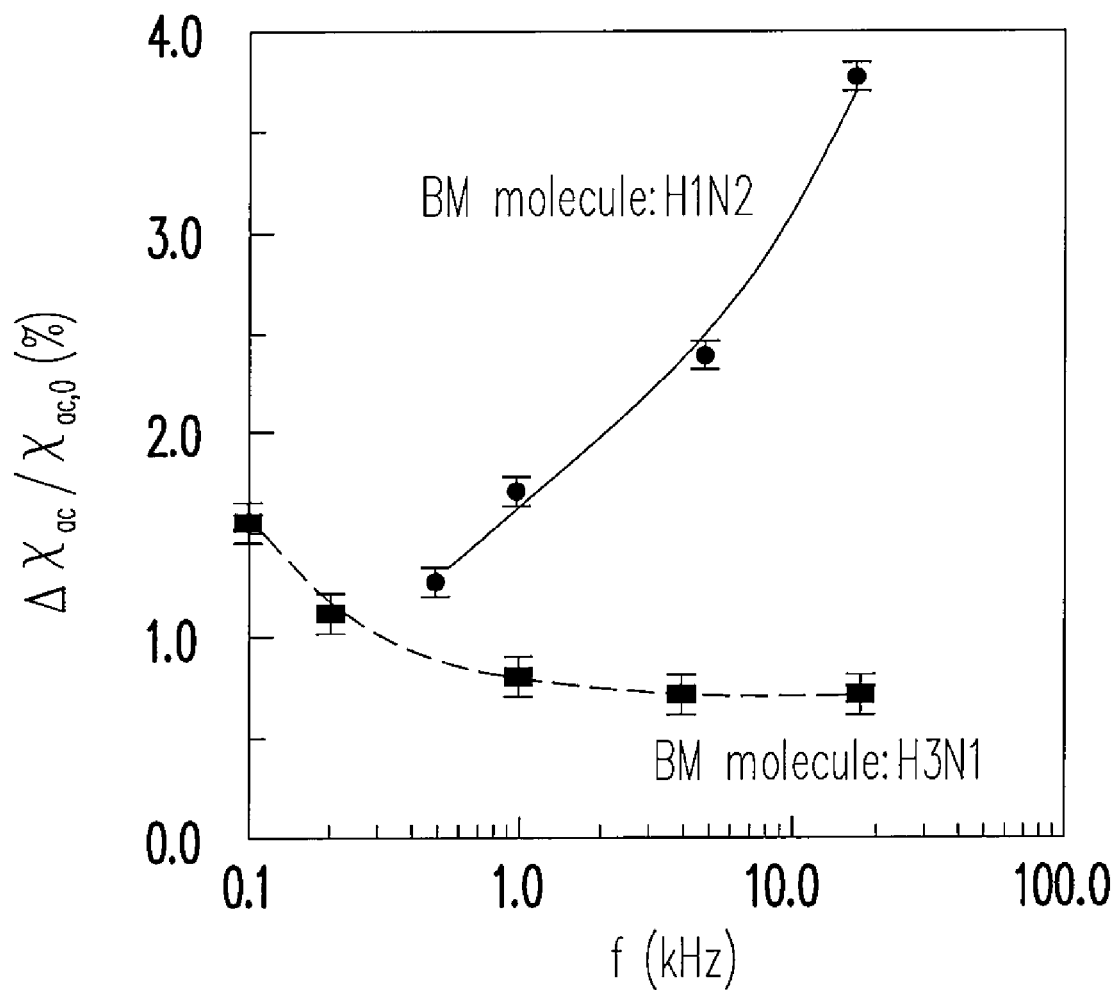
Figure 5:
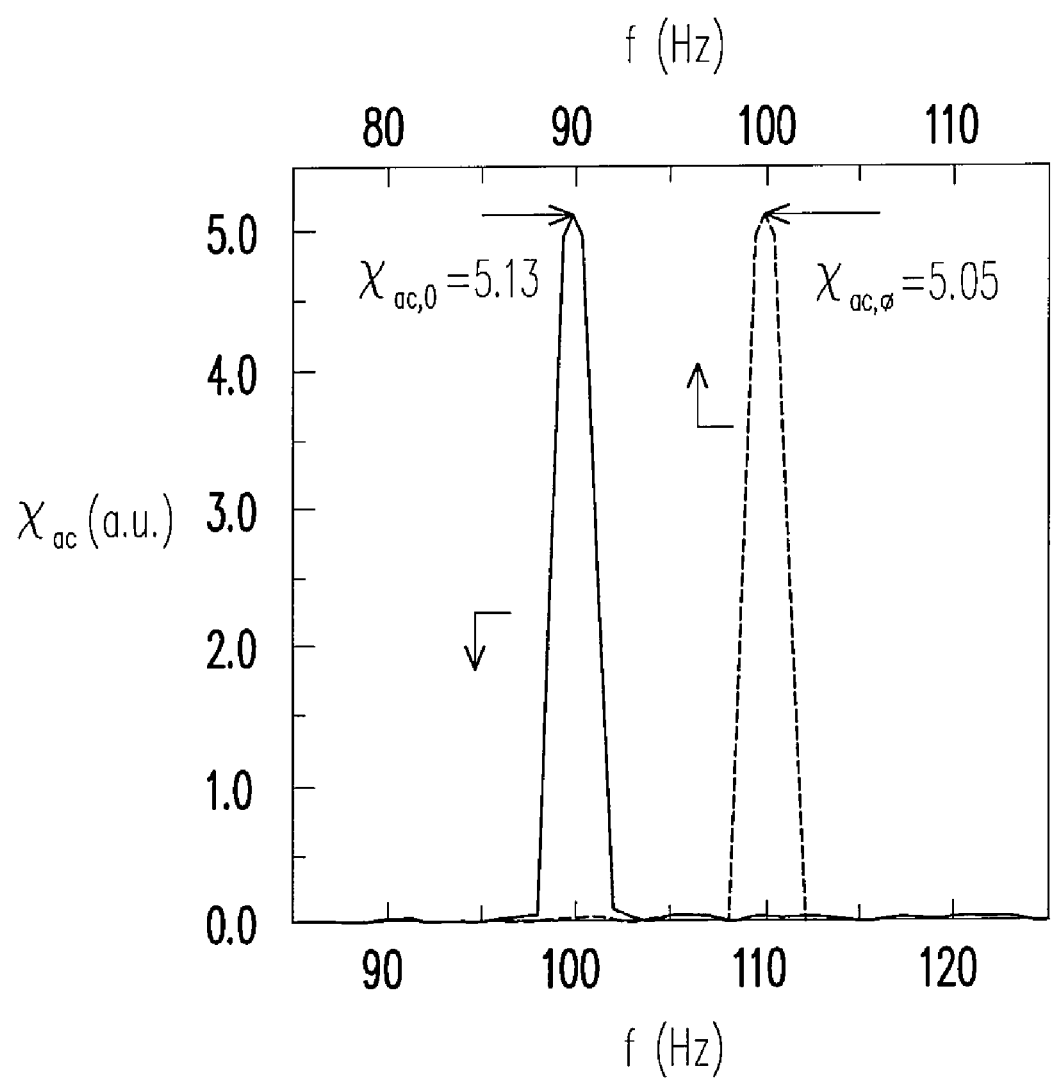

FIGS. 3-5 are drawings, schematically illustrating the phenomena in relation of $\chi_{ac}$ with the specific binding molecules and non-specific binding molecules. In FIG. 3, it is found that the $\chi_{ac,o}$ is 37.5 (solid line) shown in FIG. 3. After the formation of the specific binding between anti-H1N2 and H1N2, the magnetic susceptibility (referred as $\chi_{ac,\phi}$) of sample is found as 37.0 (dashed line). It is found that the magnetic susceptibility of sample is reduced after the formation of the specific binding between anti-H1N2 and H1N2. As can be seen, the reduction in the magnetic susceptibility of samples after the formation of immuno-complex is observed.

The magnetoreduction signal $\Delta\chi_{ac}/\chi_{ac,o}$ is obtained as 1.35%, where it is defined with $\Delta\chi_{ac}/\chi_{ac,o}=(\chi_{ac,o}-\chi_{ac,\phi})/\chi_{ac,o}\times100\%$. As the rotating frequency $f_r$ increases, the magnetoreduction signal is enhanced, as shown with the solid line in FIG. 4. The enhancement in the magnetoreduction signal at higher frequencies for the specific binding is attributed to the resonance effect of magnetic nanoparticles under forced oscillation. The results of the solid line reveal that the specific binding between anti-H1N2 and H1N2 exists from lower frequency to higher frequency.

For the non-specific binding, the BM molecule used here is, for example, H3N1, in which 40-μl and 0.1-emu/g magnetic reagent bio-functionalized with anti-H1N2 is mixed with 60-ul and 3.2-HAU/50 μl H3N1 test solution. At lower rotating frequency, such as 100 Hz, the magnetic susceptibility (referred as $\chi_{ac,o}$) of sample before the formation of the specific binding between anti-H1N2 and H3N1 is measured. It is found that the $\chi_{ac,o}$ is 5.13 (solid line) shown in FIG. 5. After the formation of the specific binding between anti-H1N2 and H3N1, the magnetic susceptibility (referred as $\chi_{ac,\phi}$)) of sample is found as $\chi_{ac,\phi}$=5.05, as shown with the dashed line in FIG. 5. It is concluded that the magnetic susceptibility of sample is reduced after the formation of the specific binding between anti-H1N2 and H3N1. The magnetoreduction signal of $\Delta\chi_{ac}/\chi_{ac,o}$ is obtained as 1.56% by the definition of $\Delta\chi_{ac}/\chi_{ac,o}=(\chi_{ac,o}-\chi_{ac,\phi})/\chi_{ac,o}\times100\%$.

In analyzing the information in FIG. 4, as the rotating frequency $f_r$ increases, the magnetoreduction signal is reduced, as shown with the dashed line in FIG. 4. The reduction in the magnetoreduction signal with increasing $f_r$ evidences that the non-specific binding between anti-H1N2 and H3N1 is suppressed at higher frequencies. The magnetoreduction signal reaches to the noise level as the rotating frequency increases to 4 kHz. This indicates that the non-specific binding between anti-H1N2 and H3N1 effectively vanishes as the rotating frequency beyond 4 kHz.

In the present invention, several curves with various binding molecules can be measured separately. Each curve is not necessarily to represent a single kind of binding molecules. In general, for example, it is divided into two types of molecules as the specific binding molecules and non-specific binding molecules. The unwanted non-specific binding molecules are to be suppressed while the wanted specific binding molecules can remain or even increased. For example, after separate curves have been obtained, an operation frequency level can be determined. In the example of FIG. 4, the operation frequency level can be, for example, set at 10 kHz, at which the non-specific molecules of H3N1 are substantially suppressed while the wanted binding molecules of H1N2 are significantly increased.

It should be noted that the measurement of $\chi_{ac}$ is not necessary to be restricted to the provided embodiments. The measurement of $\chi_{ac}$ is to describe that the actual frequency level can be determined by measuring the quantity of $\chi_{ac}$ or its related quantity. In other words, the measurement of $\chi_{ac}$ is just a tool to determine the proper frequency level. Any proper measuring mechanism to sufficiently measure the $\chi_{ac}$ can be used.

One of applications using the magnetically driven suppression in non-specific binding between molecules is the immunomagnetic separation for specific molecules. For example, a mixture includes several kinds of molecules. One can, for example, separate a specific kind of molecule from the mixture through the following processes. The coating molecules conjugated to the to-be-separated molecules are coated onto magnetic particles dispersed in water. The magnetic liquid is mixed with the mixture, followed by suppressing bindings between magnetic particles and unwanted molecules in the mixture by utilizing the magnetically driven suppression in non-specific binding developed in this invention. The specific kind of molecules is extracted from the mixture through immunomagnetic separation. Thus, only the specific kind of molecules is extracted from the mixture.

It will be apparent to those skilled in the art that various modifications and variations can be made to the structure of the present invention without departing from the scope or spirit of the invention. In view of the foregoing descriptions, it is intended that the present invention covers modifications and variations of this invention if they fall within the scope of the following claims and their equivalents.

What is claimed is:

1. A method for suppressing non-specific bindings between molecules, the method comprising:
   providing magnetic particles dispersed in a liquid, each of the magnetic particles having a magnetization;
   coating the magnetic particles with coating molecules;
   applying binding molecules mixed of first-type binding molecules and second-type binding molecules to the liquid, wherein the coating molecules are specifically binding with the first-type binding molecules and non-specifically binding with the second-type binding molecules; and
   applying an alternating current (ac) magnetic field with a frequency level, wherein the frequency level causes suppression of the second-type binding molecules in binding with the coating molecules,
   wherein the frequency level of the ac magnetic field is determined by:
   measuring a first ac magnetoreduction signal for the specific binding of the first-type binding molecules under an ac magnetic field varying in a first ac frequency range;
   measuring a second ac magnetoreduction signal for the non-specific binding of the second-type binding molecules under an ac magnetic field varying a second ac frequency range; and
   determining the frequency level, according to quantities of the first ac magnetoreduction signal and the second ac magnetoreduction signal in varying with frequency, so that the non-specific binding of the second-type binding molecules is suppressed and the specific binding of the first-type binding molecules is retained.

2. The method of claim 1, wherein the magnetic particles comprise magnetic cores and surfactant layers respectively enclose the magnetic cores.

3. The method of claim 1, wherein the step of applying the ac magnetic field comprises:
   providing a solenoid coil;
   applying an ac current through the solenoid coil; and
   disposing a container holding the liquid with the magnetic particles within the solenoid coil.

4. The method of claim 1, wherein the mechanism to suppress the second-type binding molecules in binding with the coating molecules is the centrifugal force induced by ac magnetic field(s).

5. The method of claim 1, wherein the steps of measuring the first ac magnetoreduction signal and the second ac magnetoreduction signal comprises picking signal of susceptibility by:
   providing a first-part solenoid coil and a second-part solenoid coil;
   connecting the first-part solenoid coil with the second-part solenoid coil in opposite winding direction as a pick-up coil for sensing ac susceptibility; and
   disposing a container holding the liquid with the magnetic particles inside either of the first-part or the second-part of solenoid.

6. The method of claim 5, wherein the first-part solenoid coil and the second-part solenoid coil are substantially identical.

7. A magnetic separation method, the method comprising:
   providing magnetic particles dispersed in a liquid, each of the magnetic particles having a magnetization;
   coating the magnetic particles with coating molecules;
   applying the magnetic particles with the coating molecules to a mixture having several kinds of molecules, wherein the coating molecules have a specific binding with to-be-separated molecules and have a non-specific binding with other kinds of the molecules;
   applying an alternating current (ac) magnetic field with a frequency level on the mixture, wherein the frequency level is determined by:
   measuring a first ac magnetoreduction signal for the specific binding of the to-be-separated molecules under an ac magnetic field varying in a first ac frequency range;
   measuring a second ac magnetoreduction signal for the non-specific binding of the other kinds of the molecules under an ac magnetic field varying a second ac frequency range; and
   determining the frequency level, according to quantities of the first ac magnetoreduction signal and the second ac magnetoreduction signal in varying with frequency, so that the non-specific binding of the other kinds of the molecules is suppressed and the specific binding of the to-be-separated molecules is retained; and
   extracting the to-be-separated molecules from the mixture through magnetic separation.

8. The method of claim 7, wherein the magnetic particles comprise magnetic cores and surfactant layers respectively enclose the magnetic cores.

9. The method of claim 7, wherein the mechanism to suppress the non-specific binding of the other kinds of the molecules is the centrifugal force induced by ac magnetic field(s).

10. The method of claim 7, wherein the steps of measuring the first ac magnetoreduction signal and the second ac magnetoreduction signal comprises picking signal of susceptibility by:
  providing a first-part solenoid coil and a second-part solenoid coil;
  connecting the first-part solenoid coil with the second-part solenoid coil in opposite winding direction as a pick-up coil for sensing ac susceptibility; and
  disposing a container holding the liquid with the magnetic particles inside either of the first-part or the second-part of solenoid.

11. The method of claim 10, wherein the first-part solenoid coil and the second-part solenoid coil are substantially identical.

* * * * *